| United States Patent [19] | [11] Patent Number: 4,508,906 |
|---|---|
| Bamberg et al. | [45] Date of Patent: Apr. 2, 1985 |

[54] 3-AMINO-4-(2-PYRIDYLOXY)PHENOX-YALKANOIC AND ALKENOIC ACID ESTERS

[75] Inventors: Joe T. Bamberg, Redwood City; Gustave K. Kohn, Palo Alto, both of Calif.

[73] Assignee: Zoecon Corporation, Palo Alto, Calif.

[21] Appl. No.: 581,859

[22] Filed: Feb. 21, 1984

Related U.S. Application Data

[63] Continuation-in-part of Ser. No. 430,057, Sep. 30, 1982, abandoned.

[51] Int. Cl.$^3$ .................. C07D 213/64; A01N 43/40
[52] U.S. Cl. .................. 546/300; 546/157; 546/287; 546/288; 546/296; 546/297; 544/354; 548/166; 548/221; 560/39; 260/465 D
[58] Field of Search ............... 546/288, 296, 297, 300, 546/287

[56] References Cited

U.S. PATENT DOCUMENTS

| 4,133,675 | 1/1979 | Schurter et al. | 71/94 |
| 4,216,007 | 8/1980 | Nishiyama et al. | 71/94 |
| 4,408,076 | 10/1983 | Lee | 568/325 |
| 4,448,966 | 5/1984 | Lee | 546/302 |

FOREIGN PATENT DOCUMENTS

WO81/00563 3/1981 PCT Int'l Appl. .................. 71/94

OTHER PUBLICATIONS

March, Advanced Organic Chemistry: Reactions, Mechanisms and Structure, pp. 495–496, McGraw-Hill Pub., First Edition, 1968.
March, Advanced Organic Chemistry, Reactions, Mechanisms and Structure, Second Edition, McGraw-Hill Pub., pp. 462–463, 1977.

*Primary Examiner*—Alan L. Rotman
*Attorney, Agent, or Firm*—Hana Dolezalova; Jacqueline Larson

[57] ABSTRACT

3-Amino-4-substituted phenoxy alkanoic (alkenoic) acid esters, derivatives thereof, and the use thereof for the control of weeds.

10 Claims, No Drawings

3-AMINO-4-(2-PYRIDYLOXY)PHENOXYALK-ANOIC AND ALKENOIC ACID ESTERS

This is a continuation-in-part of Ser. No. 430,057, filed Sept. 30, 1982, now abandoned.

This invention relates to novel 3-amino 4-substituted phenoxy alkanoic (alkenoic) acid esters, derivatives thereof, and the use thereof for the control of weeds.

The novel compounds of the present invention are represented by the following formulas (A) and (B):

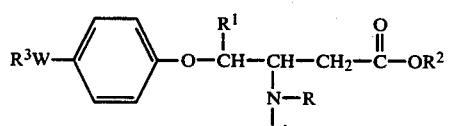  (A)

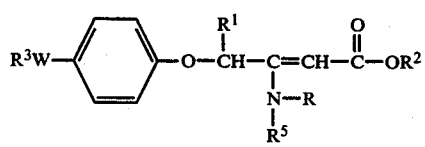  (B)

wherein,
R is hydrogen, lower alkyl or aryl;
$R^1$ is hydrogen or lower alkyl;
$R^2$ is lower alkyl, lower alkenyl or lower alkynyl;
$R^4$ is hydrogen, lower alkyl or aryl;
$R^5$ is lower alkyl or aryl;
W is oxygen, sulfur or amino; and
$R^3$ is one of the groups

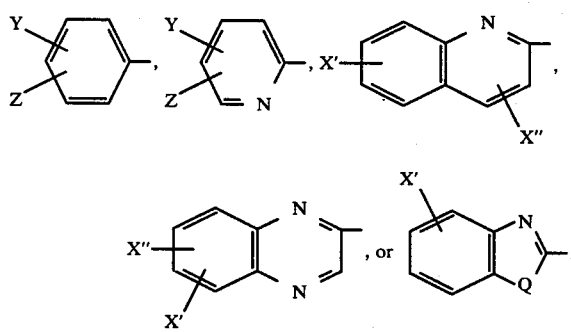

in which,
each of Y and Z is independently selected from hydrogen, lower alkyl, lower haloalkyl, lower alkoxy, lower haloalkoxy, bromo, chloro, fluoro, nitro and cyano;
each of X' and X" is independently selected from hydrogen, fluoro, chloro, bromo, trifluoromethyl, methoxy or nitro, provided that both X' and X" cannot be trifluoromethyl, methoxy or nitro; and
Q is oxygen or sulfur.

In the description and claims hereinafter, each of $R-R^5$, Q, W, X', X", Y and Z is as defined above, unless otherwise specified.

The compounds of formula (A) wherein each of R and $R^4$ is hydrogen can be prepared by the reaction of ammonia with the unsaturated compound of formula (I) at low temperature, under nitrogen, in a solvent such as ethanol. Substituted amino compounds of formula (A) wherein R and/or $R^4$ is other than hydrogen can be prepared by treatment of the unsaturated compound (I) with the appropriate amine ($RR^4NH$).

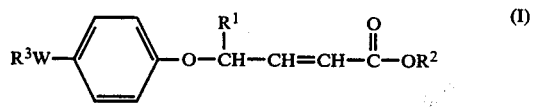  (I)

The compounds of formula (B) can be prepared by the reaction of the appropriate amine such as ethylamine, isopropylamine, aniline, and the like with a 3-oxo compound of formula (II) in a solvent such as benzene.

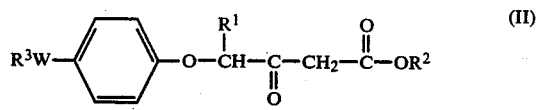  (II)

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "aryl" refers to phenyl and a substituted phenyl group such as p-methylphenyl and p-chlorophenyl.

The novel compounds of formula (A) and (B) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broad-spectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

To a solution of ethyl 4-[4-(4-trifluoromethylphenoxy)phenoxy]-2-pentenoate (0.8 g) in ethanol (25 ml), chilled in an ice bath and under nitrogen, ammonia is flowed over for about 10 minutes while stirring. Reaction is allowed to warm to R.T. The reaction is again chilled and additional ammonia added for about 15 minutes. Reaction is allowed to rise to R.T. and stirring continued over night. Reaction is concentrated under vacuum to an oil. The oily concentrate is purified by prep. thin layer chromatography using ethyl acetate/hexane (1:1) to give ethyl 4-[4-(4-trifluoromethylphenoxy)phenoxy]-3-aminopentanoate (purity 93.7%, structure confirmed by MS).

EXAMPLE 2

Using the procedure of Reynolds and Hauser, *Org. Syn. Coll.* Vol 3, a mixture of ethyl 4-[4-(4-trifluoromethylphenoxy)phenoxy]-3-oxopentanoate (1.51 g), benzene (15 ml) and aniline (0.5 g) is azeotropically distilled. The reaction product is purified using a florisil column and eluting with hexane/ethylacetate (9:1) to yield (fractions 2, 3 and 4) ethyl 4-[4-(4-trifluoromethylphenoxy)phenoxy]-3-phenylamino-2-pentenoate.

EXAMPLE 3

To a solution of ethyl 4-[4-(4-trifluoromethylphenoxy)phenoxy]-2-pentenoate (0.8 g) in ethanol (20 ml) is added 10 ml of a 40% solution of dimethylamine in water. The reaction mixture is stirred overnight at R.T. and then worked up as in Example 1 to yield the dimethylamino compound (III; R is methyl, $R^2$ is ethyl, $R^3$ is 4-trifluoromethylphenyl, $R^4$ is methyl).

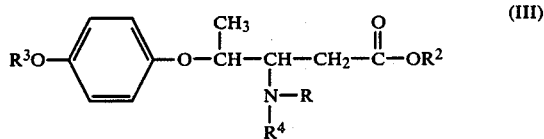
(III)

Aqueous ethylamine (70%) is used in the foregoing procedure to yield the ethylamino compound (III, R is hydrogen, $R^2$ is ethyl, $R^3$ is 4-trifluoromethylphenyl, $R^4$ is ethyl).

EXAMPLE 4

Following the procedure of Example 1, each of ethyl 4-[4-(5-trifluoromethyl-2-pyridyloxy)phenoxy]-2-pentenoate and ethyl 4-[4-(3-chloro-5-trifluoromethyl-2-pyridyloxy)phenoxy]-2-pentenoate is reacted with ammonia to give, respectively, ethyl 4-[4-(5-trifluoromethyl-2-pyridyloxy)phenoxy]-3-aminopentanoate, and ethyl 4-[4-(3-chloro-5-trifluoromethyl-2-pyridyloxy)phenoxy]-3-aminopentanoate.

EXAMPLE 5

Following the procedure of Example 2, ethyl 4-[4-(5-trifluoromethyl-2-pyridyloxy)phenoxy]-3-oxopentanoate is reacted with each of aniline, ethylamine and dimethylamine to yield, respectively, ethyl 4-[4-(5-trifluoromethyl-2-pyridyloxy)phenoxy]-3-anilino-2-pentenoate, ethyl 4-[4-(5-trifluoromethyl-2-pyridyloxy)phenoxy]-3-ethylamino-2-pentenoate, and ethyl 4-[4-(5-trifluoromethyl-2-pyridyloxy)phenoxy]-3-dimethylamino-2-pentenoate.

In the same manner, ethyl 4-[4-(3-chloro-5-trifluoromethyl-2-pyridyloxy)phenoxy]-3-oxopentanoate and ethylamine are reacted together to give ethyl 4-[4-(3-chloro-5-trifluoromethyl-2-pyridyloxy)phenoxy]-3-ethylamino-2-pentenoate.

EXAMPLE 6

Following the procedure of Example 3, each of aniline, ethylamine and dimethylamine is reacted with ethyl 4-[4-(5-trifluoromethyl-2-pyridyloxy)phenoxy]-2-pentenoate to give, respectively, ethyl 4-[4-(5-trifluoromethyl-2-pyridyloxy)phenoxy]-3-anilinopentanoate, ethyl 4-[4-(5-trifluoromethyl-2-pyridyloxy)phenoxy]-3-ethylaminopentanoate, and ethyl 4-[4-(5-trifluoromethyl-2-pyridyloxy)phenoxy]-3-dimethylaminopentanoate.

What is claimed is:

1. A compound of the following formula (A) or (B):

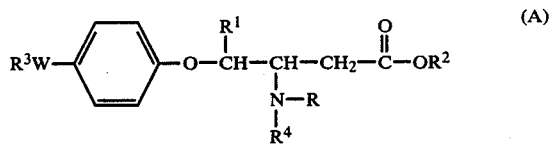
(A)

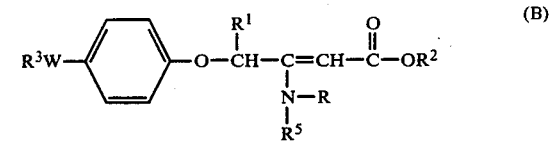
(B)

wherein,

R is hydrogen, lower alkyl or phenyl;
$R^1$ is hydrogen or lower alkyl;
$R^2$ is lower alkyl, lower alkenyl or lower alkynyl;
$R^4$ is hydrogen, lower alkyl or phenyl;
$R^5$ is lower alkyl or phenyl;
W is oxygen or sulfur; and
$R^3$ is the group in which,

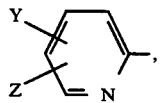

each of Y and Z is independently hydrogen, lower alkyl, lower haloalkyl, lower alkoxy, lower haloalkoxy, bromo, chloro, fluoro, nitro or cyano.

2. A compound according to claim 1 wherein $R^1$ is methyl, $R^2$ is lower alkyl, W is oxygen and $R^3$ is

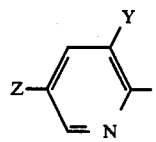

wherein Y is hydrogen or chloro and Z is chloro or trifluoromethyl.

3. A compound of formula (A) according to claim 2.

4. A compound according to claim 3 wherein R is hydrogen, methyl or ethyl and $R^4$ is hydrogen, methyl or ethyl.

5. A compound according to claim 4 wherein Y is hydrogen and Z is trifluoromethyl.

6. A compound according to claim 4 wherein Y is chloro and Z is trifluoromethyl.

7. A compound of formula (B) according to claim 2.

8. A compound according to claim 7 wherein R is hydrogen, methyl or ethyl and $R^5$ is hydrogen, methyl or ethyl.

9. A compound according to claim 8 wherein Y is hydrogen and Z is trifluoromethyl.

10. A compound according to claim 8 wherein Y is chloro and Z is trifluoromethyl.

* * * * *